(12) United States Patent
Wanasek (10) Patent No.: US 7,136,702 B2
(45) Date of Patent: **\*Nov. 14, 2006**

(54) METHOD AND APPARATUS FOR DELIVERING MULTI-DIRECTIONAL DEFIBRILLATION WAVEFORMS

(75) Inventor: Kevin A. Wanasek, Princeton, MN (US)

(73) Assignee: Medtronic, Inc., Minneapolis, MN (US)

( \* ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 48 days.

(21) Appl. No.: 10/804,322

(22) Filed: Mar. 19, 2004

(65) Prior Publication Data

US 2005/0209646 A1    Sep. 22, 2005

(51) Int. Cl.
*A61N 1/36*    (2006.01)

(52) U.S. Cl. .................. 607/5; 607/9; 607/32; 600/372; 600/373; 600/374

(58) Field of Classification Search ..................... 607/5, 607/9, 32; 600/372–374
See application file for complete search history.

(56) References Cited

U.S. PATENT DOCUMENTS

| | | | |
|---|---|---|---|
| 4,316,472 A | | 2/1982 | Mirowski et al. |
| 4,384,585 A | | 5/1983 | Zipes |
| 4,436,093 A | \* | 3/1984 | Belt ............................... 607/9 |
| 4,566,457 A | \* | 1/1986 | Stemple ......................... 607/5 |
| 4,587,970 A | | 5/1986 | Holley et al. |
| 4,614,192 A | \* | 9/1986 | Imran et al. .................... 607/5 |
| 4,641,656 A | | 2/1987 | Smits |
| 4,708,145 A | | 11/1987 | Tacker et al. |
| 4,726,379 A | \* | 2/1988 | Altman et al. .................. 607/9 |
| 4,726,380 A | | 2/1988 | Vollmann et al. |
| 4,727,877 A | | 3/1988 | Kallok |
| 4,830,006 A | | 5/1989 | Haluska et al. |
| 4,850,357 A | | 7/1989 | Bach |
| 4,932,407 A | | 6/1990 | Williams |
| 4,949,719 A | | 8/1990 | Pless et al. |
| 4,953,551 A | | 9/1990 | Mehra et al. |
| 4,998,531 A | | 3/1991 | Bocchi et al. |
| 5,107,834 A | | 4/1992 | Ideker et al. |
| 5,117,824 A | | 6/1992 | Keimel et al. |
| 5,163,427 A | | 11/1992 | Keimel |
| 5,188,105 A | | 2/1993 | Keimel |
| 5,411,524 A | | 5/1995 | Rahul |
| 5,468,254 A | | 11/1995 | Hahn et al. |

(Continued)

OTHER PUBLICATIONS

Pagan-Carlo MD et al. "Encircling Overlapping Multipulse Shock Waveforms for Transthoracic Defibrillation" *J of Am Coll Cardio*. Dec. 1998;vol. 32 Issue 7:pp. 2065-2071.

*Primary Examiner*—Robert E. Pezzuto
*Assistant Examiner*—Deborah Malamud
(74) *Attorney, Agent, or Firm*—Michael C. Soldner; Girma Wolde-Michael (57) ABSTRACT

A method and apparatus for delivering a pulse waveform to a target site of a patient that includes an energy storage device storing electrical energy and control circuitry, coupled to the energy storage device and a plurality of electrodes, generating the pulse waveform from the stored energy and delivering the pulse waveform to the target site via the plurality of electrodes. Each of the electrodes includes a pair of switching elements that are selectively opened and closed by the control circuitry in response to control signals to produce pulse signals at each output terminal. Continuous multi-directional waveforms are formed by generating phase-shifted signals at each electrode.

24 Claims, 8 Drawing Sheets

U.S. PATENT DOCUMENTS

| | | | |
|---|---|---|---|
| 5,584,865 A * | 12/1996 | Hirschberg et al. | 607/5 |
| 5,653,740 A | 8/1997 | Degroot et al. | |
| 5,814,076 A * | 9/1998 | Brownlee | 607/9 |
| 5,865,838 A * | 2/1999 | Obel et al. | 607/5 |
| 5,921,923 A * | 7/1999 | Kuck et al. | 600/373 |
| 6,085,117 A * | 7/2000 | Griffin et al. | 607/5 |
| 6,091,988 A | 7/2000 | Warman et al. | |
| 6,178,351 B1 * | 1/2001 | Mower | 607/5 |
| 6,449,506 B1 * | 9/2002 | Sh. Revishvili et al. | 607/5 |
| 6,647,292 B1 | 11/2003 | Bardy et al. | |
| 6,671,546 B1 * | 12/2003 | Cansell et al. | 607/5 |
| 6,735,472 B1 * | 5/2004 | Helland | 607/5 |
| 6,909,916 B1 * | 6/2005 | Spinelli et al. | 607/9 |
| 2002/0095187 A1 | 7/2002 | Thompson et al. | |
| 2005/0209647 A1 * | 9/2005 | Wanasek et al. | 607/5 |

\* cited by examiner

METHOD AND APPARATUS FOR DELIVERING MULTI-DIRECTIONAL DEFIBRILLATION WAVEFORMS

RELATED APPLICATION

Cross-reference is hereby made to commonly assigned related U.S. applications Ser. No. 10/804,780, filed concurrently herewith, entitled "METHOD AND APPARATUS FOR DELIVERING MULTI-DIRECTIONAL DEFIBRILLATION WAVEFORMS", incorporated herein by reference in its entirety.

FIELD OF THE INVENTION

The present invention relates generally to cardiac defibrillation devices and, more specifically, to a system and method for defibrillating the heart using multiple-pathway, simultaneously delivered phase-shifted or stepped waveforms for achieving a multi-directional defibrillation vector field.

BACKGROUND OF THE INVENTION

Implantable systems for delivering high-energy shocks to defibrillate the heart conventionally use a number of electrodes to deliver single or multiple simultaneous or sequential defibrillation waveforms. A current pathway between two electrodes is referred to as a current vector. A single current vector, for example, between an electrode located in the right ventricle and an electrode placed outside the right ventricle, occasionally results in undesirably high energy levels being required in order to effectively defibrillate the heart (defibrillation threshold). In delivering a defibrillation shock, it is desirable to deliver the energy in a vector substantially parallel to a large mass of the cardiac myocytes in order to simultaneously depolarize the myocytes and "reset" them, thereby restoring normal sinus rhythm. This shock directionality is approximated through the positioning of defibrillation electrodes relative to the heart. However, because the cardiac structure is complex, a defibrillation pathway selected between two defibrillation coil electrodes, between a defibrillation coil electrode and the implantable device housing used as a "CAN" defibrillation coil electrode and the implantable device housing used as a "CAN" electrode, or between a defibrillation coil electrode and a subcutaneous patch electrode, may be substantially parallel to only some of the cells.

In an effort to reduce the amount of energy required to effect defibrillation, numerous suggestions have been made with regard to multiple electrode systems. For example, sequential pulse multiple electrodes systems are generally disclosed in U.S. Pat. No. 4,708,145 issued to Tacker et al., U.S. Pat. No. 4,727,877 issued to Kallok et al., U.S. Pat. No. 4,932,407 issued to Williams et al., and U.S. Pat. No. 5,163,427 issued to Keimel.

An alternative approach to multiple electrode sequential pulse defibrillation is disclosed in U.S. Pat. No. 4,641,656 to Smits and also in the above-cited Williams patent. An alternative multiple electrode, simultaneous pulse system is disclosed in U.S. Pat. No. 4,953,551, issued to Mehra et al., employing right ventricular, superior vena cava and subcutaneous patch electrodes.

Pulse waveforms delivered either simultaneously or sequentially to multiple electrode systems may be monophasic (either of positive or negative polarity), biphasic (having both a negative-going and positive-going pulse), or multiphasic (having two or more polarity reversals). Such waveforms thus include one or more pulses of negative and/or positive polarity that are typically truncated exponential pulses. While the term "multiphasic" is used to refer to a pulse waveform having two or more polarity reversals, the waveform may be described as a "multiple pulse" waveform that includes both positive and negative pulses with intervening pulse delays. These monophasic, biphasic, and multiphasic pulse waveforms are achieved by controlling the discharge of a capacitor or bank of capacitors during shock delivery.

Simultaneous multiple electrode defibrillation configurations provide a defibrillation pathway along more than one vector simultaneously producing a net vector field. However, in multiple electrode configurations, each pathway or vector will have an associated resistance. When multiple pathways are used simultaneously, a current divider effect is created. The path with the least resistance will receive the majority of the defibrillation shock current.

In sequential multiple electrode configurations, a defibrillation waveform is typically delivered along two current pathways sequentially such that one defibrillation vector is produced followed by a second defibrillation vector. The directionality of the sequential vectors is generally limited to two distinct vectors determined by the location of the electrodes used to deliver each pulse. Even when using multiple electrode configurations, a relatively high-energy shock is still required in order to successfully defibrillate the heart.

Reducing device size to an acceptable implantable size was a major obstacle in realizing the first implantable defibrillation devices. Large battery and capacitor requirements for delivering high-energy shock pulses required early devices to be relatively large. Using biphasic truncated exponential waveforms for internal cardiac defibrillation via transvenously positioned electrodes has allowed defibrillation thresholds to be reduced to the point that device size is acceptable for pectoral implant. However, relatively high energy requirements still continue to limit device longevity and size reduction, both of which continue to be motivating factors to improve implantable defibrillation systems by reducing the defibrillation thresholds required to successfully defibrillate the heart. Reduced defibrillation energy may be accompanied by reduced sensitivity to lead placement and differences in cardiac anatomy and thereby reduce the number of patients in which unacceptable defibrillation thresholds are encountered.

As discussed previously, reduction in defibrillation thresholds may be achievable if a greater number of the cardiac myocytes are parallel to the defibrillation vector field. One approach to addressing this need could be to increase the number of electrodes to allow delivery of simultaneous or sequential defibrillation pulses along a greater number of vectors. Placement of additional electrodes however, adds size, cost, and complexity to the implanted system and would make implantation of the system an arduous task.

There remains a need, therefore, for an improved system and method for defibrillating the heart using a multi-directional defibrillation vector field for achieving successful defibrillation at lower shock energies and that allows a reduction in implantable device size and/or extension of the useful life of the implanted device. By reducing the defibrillation energy required, the number of patients in which acceptable defibrillation thresholds are unachievable may also be reduced.

BRIEF DESCRIPTION OF THE DRAWINGS

Aspects and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

The present invention is directed toward providing a system and method for cardioverting or defibrillating the heart using a defibrillation waveform that includes multiple signals delivered simultaneously to multiple electrode pathways to create a dynamically varying, multi-directional defibrillation vector field. The defibrillation waveform may be composed of continuous, phase-shifted signals delivered simultaneously to multiple electrode pathways to achieve a continuous or "sweeping" multi-directional vector field.

"Cardioversion" typically refers to the termination of tachycardia, and "defibrillation" typically refers to the termination of fibrillation. When not stated otherwise, the terms "defibrillation" and "defibrillator" are intended to include "cardioversion" and "cardioverter", respectively, in that the multi-directional defibrillation waveforms produced in accordance with the present invention may be duly used whenever a high-energy shock therapy is required, including both cardioversion and defibrillation shock therapies.

The present invention reduces defibrillation thresholds, improves defibrillation success rate, reduces sensitivity to electrode location, and results in fewer cases of unattainable acceptable defibrillation thresholds. In one embodiment, the present invention is implemented in an implantable cardiac defibrillation device. The overall device size may be reduced by reducing battery and capacitor size, thereby allowing for greater patient comfort and acceptance, and/or the useful life of the implantable device may be extended due to reduced defibrillation thresholds. A reduction in defibrillation thresholds which reduces the delivered voltage requirements of the device reduces space requirements for implementing output circuitry. The standoff voltage required in output circuitry of currently available high-voltage devices requires a relatively large amount of the available volume within the implantable device. Utilizing the present invention t reduce the delivered voltage requirements will reduce the space requirements for the output circuitry, allowing overall device size reduction or allowing increased battery size, memory size or other device enhancements. Implantable systems in which the present invention may be usefully practiced include single, dual or multi-chamber systems used for defibrillating the atrial and/or the ventricular heart chambers.

Multi-chamber implantable systems will be described in detail herein to illustrate various embodiments of the present invention. The advantages provided by the present invention, however, can also be beneficial in external defibrillation systems. As such, aspects of the present invention may be advantageously employed in external defibrillation systems utilizing cutaneous or transcutaneous electrode systems.

Figure 1A:
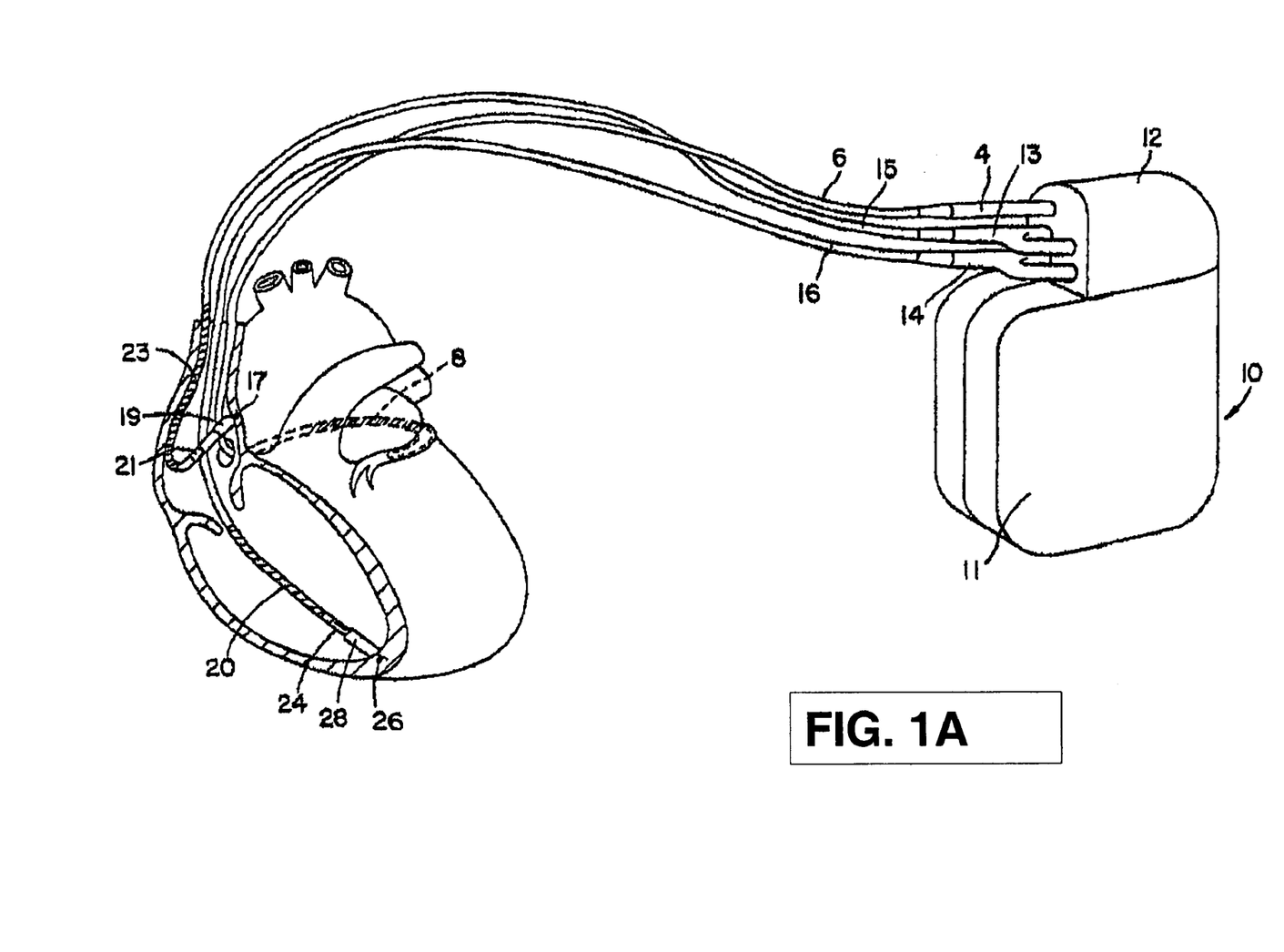
FIG. 1A is an illustration of an exemplary implantable cardiac stimulation device coupled to transvenous leads.

FIG. 1A is an illustration of an exemplary implantable cardiac stimulation device in which the present invention may be practiced. Device 10 is provided with multi-chamber pacemaking, cardioversion, and defibrillation capabilities and is coupled to a patient's heart by way of multiple leads. For example, a connector block 12 receives the proximal end of a right ventricular lead 16, a right atrial lead 15 and a coronary sinus lead 6, used for positioning electrodes for sensing and stimulation in three or four heart chambers.

In FIG. 1A, the right ventricular lead 16 is positioned such that a distal end is in the right ventricle (RV) for sensing right ventricular cardiac signals and delivering pacing or shocking pulses in the right ventricle. For these purposes, right ventricular lead 16 includes a ring electrode 24, a tip electrode 26, optionally mounted retractably within an electrode head 28, and an RV coil electrode 20, each of which are connected to an insulated conductor contained within the body of lead 16. The proximal end of the insulated conductors are coupled to corresponding connectors carried by connector 14 at the proximal end of lead 16 for providing electrical connection to the device 10, referred to hereafter as "implantable cardioverter defibrillator" or "ICD".

The right atrial lead 15 is positioned such that a distal end is in the vicinity of the right atrium and the superior vena cava (SVC). Lead 15 includes a ring electrode 21 and a tip electrode 17, optionally mounted retractably within electrode head 19, for sensing and pacing in the right atrium. Lead 15 further includes an SVC coil electrode 23 for delivering high-energy shock therapy. The ring electrode 21, the tip electrode 17 and the SVC coil electrode 23 are each connected to an insulated conductor with the body of the right atrial lead 15. Each insulated conductor is coupled at a proximal end to a connector carried by connector 13.

The coronary sinus (CS) lead 6 is advanced within the vasculature of the left side of the heart via the coronary sinus and great cardiac vein and may be advanced further into a deeper cardiac vein. The coronary sinus lead 6 is shown in the embodiment of FIG. 1A as having a defibrillation coil electrode 8 that may be used in combination with either or both the RV coil electrode 20 or the SVC coil electrode 23 for delivering electrical shocks for cardioversion and defibrillation therapies. The device housing 11 may also serve as a subcutaneous defibrillation electrode in combination with two or more of the defibrillation coil electrodes 8, 20 or 23 for defibrillation of the atria and/or ventricles. In other embodiments, CS lead 6 may also include a distal tip electrode and ring electrode for pacing and sensing functions in the left chambers of the heart. The CS coil electrode 8 is coupled to an insulated conductor within the body of lead 6, which provides connection to the proximal connector 4.

It is recognized that alternate lead systems may be substituted for the three lead system illustrated in FIG. 1A. The present invention employs at least three electrodes for delivering a phase-shifted or stepped defibrillation waveform for achieving a dynamically-varying multi-directional vector field. While three coil electrodes 8, 20 and 23 shown in FIG. 1A are each located on separate leads, other lead systems could be substituted that include two or more defibrillation coils on a single lead. For example, a quadrapolar lead having an RV tip electrode, an RV ring electrode, an RV coil electrode and an SVC coil electrode may be used.

The approximate positions of electrodes 8, 20 and 23 and can 11 as shown in FIG. 1A are illustrative. Multiple electrode pathways for delivering defibrillation waveforms in accordance with the present invention may be selected between coil electrodes 8, 20 and 23, or may alternatively include can 11 in combination with two or three of the coil electrodes 8, 20 or 23. In some embodiments, can 11 may be electrically coupled to the same potential as one of the coil electrodes 8, 20 or 23. When 3-electrode configurations are used, the triangle formed by the three electrodes preferably encompasses a large volume of the targeted cardiac chamber(s).

According to another embodiment of the present invention, an electrode configuration including RV coil 20, can 11, CS coil 8 and/or a coronary vein (CV) coil electrode could be utilized. CV coil 8 and the CV coil electrode could be utilized in conjunction with a pacing lead as electrically separate electrodes, tied together, or tied to RV coil 20 or can 11. In the dual coil configuration, a distal coil would be positioned within the coronary vein and a proximal coil would be positioned in the coronary sinus, and may be partially within the right atrium or the superior vena cava.

While a particular multi-chamber ICD and lead system is illustrated in FIG. 1A methodologies included in the present invention may be adapted for use with other single chamber, dual chamber, or multichamber ICD systems involving multiple defibrillation electrodes located within the heart or external to the heart such as epicardial or subcutaneous placements. The implementation of the present invention may also include a device that does not employ cardiac leads as described above to detect and treat arrhythmias. For example, a device implanted subcutaneously or sub-muscularly in a position over the heart such as an axillary location could use non-intracardiac lead based methods for delivering electrical stimulation therapies and sensing cardiac activity.

Figure 1B:
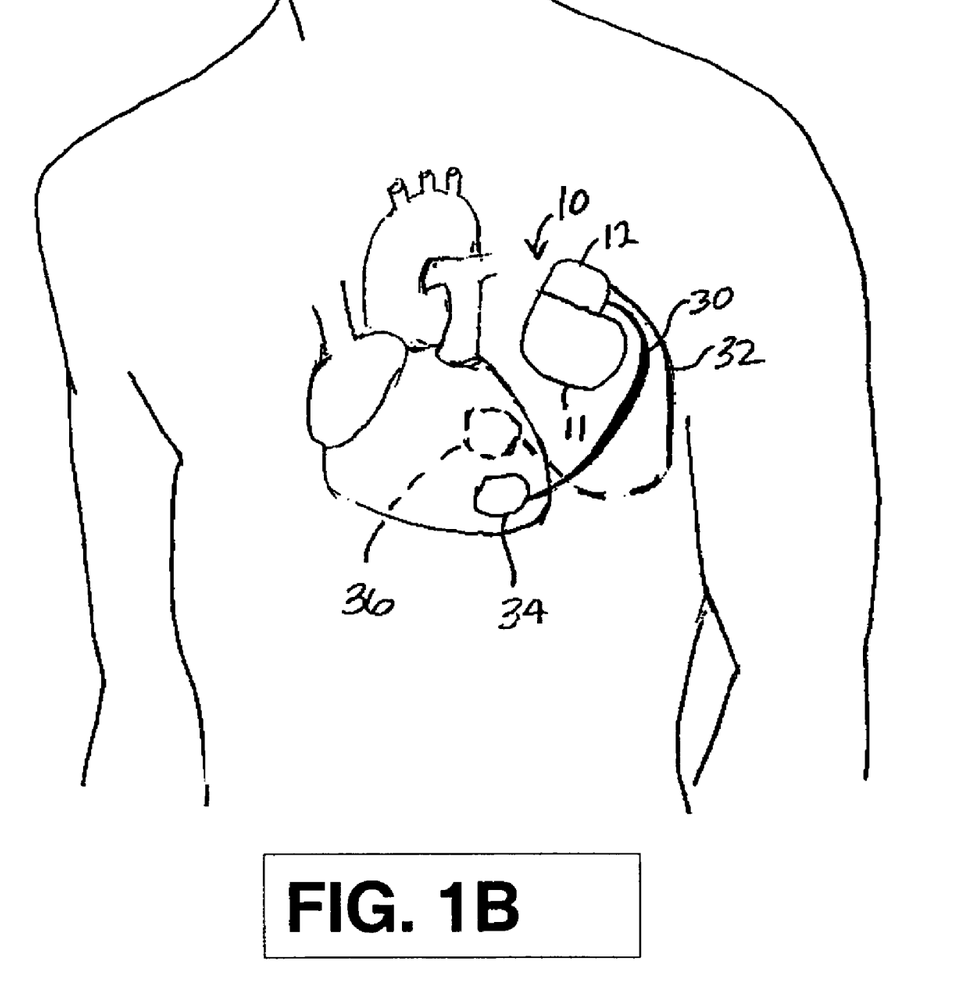
FIG. 1B is an illustration of an implantable cardiac stimulation device coupled to subcutaneous leads.

FIG. 1B is an illustration of an implantable cardiac stimulation device employing subcutaneous leads for positioning electrodes used for delivering defibrillation waveforms. In this embodiment, device 10 is coupled to two subcutaneous leads 30 and 32 coupled to subcutaneous patch electrodes 34 and 36, respectively. Subcutaneous patch electrodes 34 and 36 and device housing 11 may be positioned so that defibrillation pathways between the subcutaneous electrodes 34 and 36 and housing 11 will create an energy field encompassing a large mass of the targeted heart chambers.

In accordance with the present invention, phase-shifted defibrillation waveforms may be delivered along multiple pathways between subcutaneous electrodes 34 and 36 and housing 11 to create a multi-directional vector field. Sensing of cardiac activity may be performed using subcutaneous sensing electrodes (not shown) or electrodes incorporated on housing 11. It is recognized that additional electrodes dedicated to pacing and/or sensing functions may be incorporated on the device housing 11, subcutaneous patches 34 and 36 or on additional subcutaneous patches, also coupled to leads 30 or 32 or separate leads.

Positioning of device 10 is not limited to the left pectoral position, shown in FIG. 1B. For example, device 10 may alternatively be implanted in a right pectoral position. If housing 11 is not used as an electrode, device 10 may be implanted abdominally.

In alternative embodiments, a hybrid system including both subcutaneous electrodes and transvenous electrodes may be used. For example, transvenous leads may be used to position electrodes within the heart for accurate sensing of cardiac activity and subcutaneous electrodes may be positioned for delivering multi-directional defibrillation waveforms. The present invention may also be implemented in leadless subcutaneous cardiac stimulation devices such as the subcutaneous implantable cardioverter defibrillator generally disclosed in U.S. Pat. No. 6,647,292, issued to Bardy et al., incorporated herein by reference in its entirety.

Figure 2:
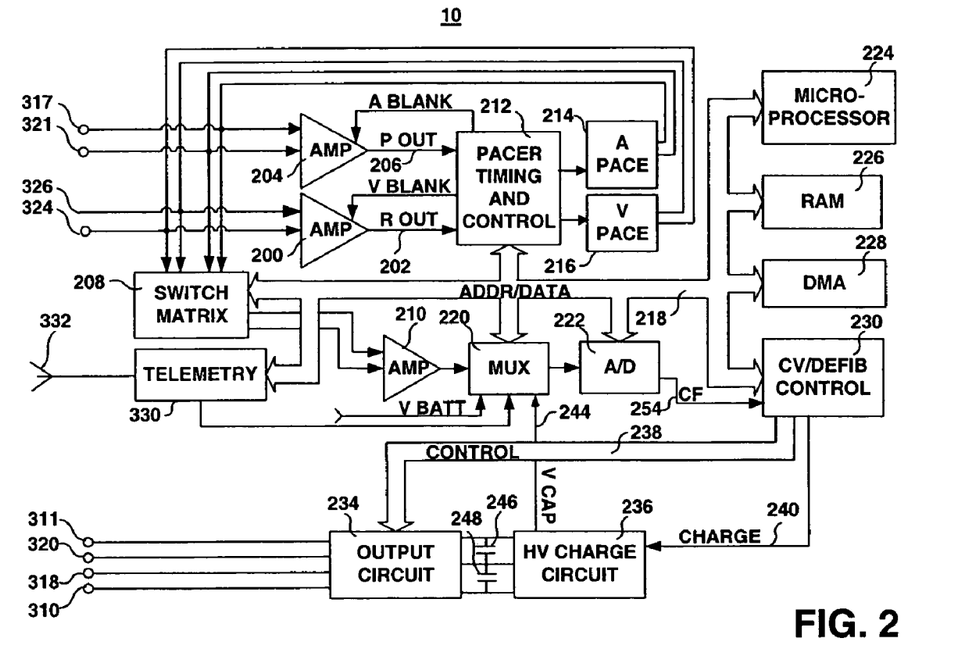
FIG. 2 is a functional block diagram of a cardiac stimulation device in which the present invention may be practiced.

FIG. 2 is a functional block diagram of the cardiac stimulation device shown in FIG. 1A. This diagram should be taken as exemplary of the type of device with which the invention may be embodied and not as limiting, as it is believed that the invention may be usefully practiced in a wide variety of device implementations. For example, the present invention may be practiced in a device intended for delivering cardioversion and/or defibrillation shocks to one or more heart chambers and may or may not include other cardiac stimulation therapy capabilities, e.g., cardiac pacing therapies. The disclosed embodiment shown in FIG. 2 is a microprocessor-controlled device, but the methods of the present invention may also be practiced with devices employing dedicated integrated circuitry for controlling device functions.

With regard to the electrode system illustrated in FIG. 1A, the ICD 10 is provided with a number of connection terminals for achieving electrical connection to the cardiac leads 6, 15, and 16 and their respective electrodes. The connection terminal 311 provides electrical connection to the housing 11 for use as an active electrode during defibrillation. The connection terminals 320, 310, and 318 provide electrical connection to coil electrodes 20, 8 and 23 respectively. Each of these connection terminals 311, 320, 310, and 318 may be located in connector block 12 and are coupled to the high voltage output circuit 234 to facilitate the delivery of high energy shocking pulses to the heart using coil electrodes 8, 20, and 23 and optionally the housing 11.

The connection terminals 317 and 321 provide electrical connection to tip electrode 17 and ring electrode 21 positioned in the right atrium. The connection terminals 317 and 321 are further coupled to an atrial sense amplifier 204 for sensing atrial signals such as P-waves. The connection terminals 326 and 324 provide electrical connection to tip electrode 26 and the ring electrode 24 positioned in the right ventricle. The connection terminals 326 and 324 are further coupled to a ventricular sense amplifier 200 for sensing ventricular signals such as R-waves.

The atrial sense amplifier 204 and the ventricular sense amplifier 200 preferably take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methods known in the art.

The telemetry circuit 330 receives downlink telemetry from and sends uplink telemetry to an external programmer, as is conventional in implantable anti-arrhythmia devices, by means of an antenna 332. Received telemetry is provided to microprocessor 224 via multiplexer 220. Data to be uplinked to the programmer and control signals for the telemetry circuit 330 are provided by microprocessor 224 via address/data bus 218. Data to be uplinked may include a record of detected and classified arrhythmia episodes as is customary in modern ICDs. Numerous types of telemetry systems known for use in implantable devices may be used.

The remainder of circuitry illustrated in FIG. 2 is dedicated to the provision of cardiac pacing, cardioversion and defibrillation therapies. In the exemplary embodiment shown in FIG. 2, the pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224. For the purposes of the present invention, pacer circuitry 212 may correspond to pacer timing and control circuitry known in the art.

Microprocessor 224 operates as an interrupt driven device and is responsive to interrupts from pacer timing and control circuitry 212 corresponding to the occurrences of sensed P-waves and R-waves and corresponding to the generation of cardiac pacing pulses. Any necessary mathematical calculations to be performed by microprocessor 224 and any updating of the values or intervals controlled by pacer timing/control circuitry 212 take place following such interrupts. A portion of the random access memory 226 may be configured as a number of recirculating buffers capable of holding a series of measured intervals, such as R—R intervals, P—P intervals and P-R intervals, which may be analyzed in response to a pace or sense interrupt by microprocessor 224 for diagnosing an arrhythmia. Any of the various arrhythmia detection methodologies known to the art may be employed for detecting ventricular and atrial arrhythmias.

In response to the detection of atrial or ventricular tachycardia, an anti-tachycardia pacing therapy may be delivered if desired by loading a regimen from microcontroller 224 into the pacer timing and control circuitry 212 according to the type of tachycardia detected. In the event that higher voltage cardioversion or defibrillation shock therapies are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors 246 and 248 is monitored via a voltage capacitor (VCAP) line 244, which is passed through the multiplexer 220. While a pair of capacitors 246 and 248 is shown in FIG. 2, the present invention may be implemented using a single high voltage capacitor or a bank of capacitors that includes two or more capacitors. When the capacitance voltage reaches a predetermined value set by microprocessor 224, a logic signal is generated on the capacitor full (CF) line 254, terminating charging. Thereafter, timing of the delivery of the defibrillation or cardioversion pulse is controlled by pacer timing and control circuitry 212.

One embodiment of an appropriate system for delivery and synchronization of ventricular cardioversion and defibrillation waveforms and for controlling the timing function related to them is generally disclosed in commonly assigned U.S. Pat. No. 5,188,105 to Keimel, incorporated herein by reference in its entirety. If atrial defibrillation capabilities are included in the device, appropriate systems for delivery and synchronization of atrial cardioversion and defibrillation waveforms and for controlling the timing function related to them may be found in U.S. Pat. No. 4,316,472 issued to Mirowski et al., U.S. Pat. No. 5,411,524 issued to Mehra, or U.S. Pat. No. 6,091,988 issued to Warman. Any known ventricular cardioversion or defibrillation control circuitry may be usable in conjunction with the present invention for controlling the timing of capacitor charging and delivery of cardioversion and defibrillation waveforms relative to sensed depolarization signals. Reference is made, for example, to U.S. Pat. No. 4,384,585, issued to Zipes and U.S. Pat. No. 4,949,719, issued to Pless et al.

In the illustrated device, delivery of cardioversion or defibrillation waveforms is accomplished by output circuit 234, under control of control circuitry 230 via control bus 238. Output circuit 234 determines the shock pulse waveform and which electrodes are involved in delivery of the shock waveform. In accordance with the present invention, output circuit 234 is provided as an output bridge including switching circuitry controlled by firmware resident in microprocessor 224 or by dedicated circuitry included in control circuit 230. As will be described in greater detail below, switching circuitry included in output circuit 234 is activated according to predetermined timing algorithms to produce phase-shifted or stepped waveforms.

In modern implantable cardioverter defibrillators, the particular therapies are programmed into the device ahead of time by the physician, and a menu of therapies is typically provided. For example, on initial detection of tachycardia, an anti-tachycardia pacing therapy may be selected. On redetection of tachycardia, a more aggressive anti-tachycardia pacing therapy may be scheduled. If repeated attempts at anti-tachycardia pacing therapies fail, a higher-level cardioversion pulse therapy may be selected thereafter. As in the case of currently available ICDs, and as discussed in the above-cited references, it is envisioned that the amplitude of the defibrillation shock waveform may be incremented in response to failure of an initial shock or shocks to terminate fibrillation. Prior art patents illustrating such pre-set therapy menus of anti-tachycardia therapies include U.S. Pat. No. 4,726,380 issued to Vollmann et al., U.S. Pat. No. 4,587,970 issued to Holley et al., and U.S. Pat. No. 4,830,006 issued to Haluska.

Figure 3A:
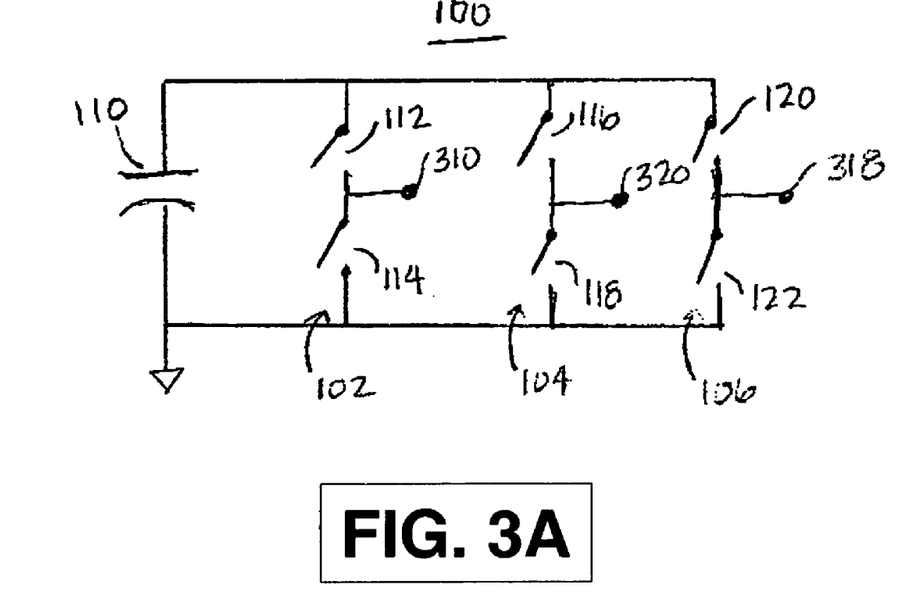
FIG. 3A is a diagram of an output bridge circuit that may be included in the cardioversion/defibrillation output circuitry shown in the device of FIG. 2, which may be used for generating a phase-shifted defibrillation waveform in accordance with the present invention for achieving a continuous multi-directional defibrillation vector field.

FIG. 3A is a diagram of an output bridge circuit that may be included in output circuit 234 for generating a phase-shifted defibrillation waveform for achieving a continuous multi-directional defibrillation vector field in accordance with the present invention. Bridge circuit 100 includes at least three legs 102, 104, and 106 coupled to a high voltage capacitor 110. Capacitor 110 may be embodied as a single capacitor element as shown in FIG. 3A or may be embodied as a bank of capacitors, including two or more capacitor elements such as the capacitors 246 and 248 shown in FIG. 2. When circuit 100 is used in conjunction with an external defibrillation device, capacitor 110 may conceivably be eliminated with the input to circuit 100 provided by line power.

Each leg 102, 104, and 106 includes a pair of switching components. Each pair is configured to include a "high" and a "low" switch for generating positive-going and negative-going pulse signals, respectively, for forming the positive- and negative-going phases of a defibrillation waveform. As will be described in greater detail below, control signals delivered to each pair of switching components 112 and 114, 116 and 118, and 120 and 122 produce a chopped waveform within a sinusoidal envelope to approximate a sinusoidal waveform at each output terminal 310, 320 and 318. In other embodiments, phasic signals may be produced by signals that ramp and decay, rise and fall exponentially, or otherwise alternate in a phasic manner.

Switching elements 112 and 114 included in leg 102 provide positive and negative going pulses, respectively, that contribute to the formation of a first signal of a phase-shifted defibrillation waveform at terminal 310, which may correspond to the SVC coil electrode terminal 310 as shown in FIG. 2. Switching elements 116 and 118 included in leg 104 provide positive and negative going pulses that form a second signal of a phase-shifted defibrillation waveform at terminal 320, which may correspond to the RV coil electrode terminal 320 shown in FIG. 2. Likewise, switching elements 120 and 122 included in leg 106 provide positive and negative going pulses that form a third signal of a phase-shifted defibrillation waveform at terminal 318, which may correspond to the CS coil electrode terminal 318 shown in FIG. 2. Alternatively, any of legs 102, 104, and 106 may be coupled to terminal 311 for using the device housing as a "CAN" electrode as described previously. In addition, any of legs 102, 104 and 106 may be coupled to two or more terminals such that two or more electrodes, for example housing 11 and SVC coil 23, are tied to the same potential during defibrillation.

Switching elements 112 through 122 may be embodied as semi-conductor elements, such as field effect transistors (FETs), insulated gate bipolar junction transistors (IGBTs), silicon controlled rectifiers (SCRs), Triac switches or other switching components for alternating the capacitor discharge signal between a high and low level to create pulses used to construct a phase-shifted defibrillation waveform. Depending on the implementation of switching elements 112 through 122, for example if SCR or Triac switches are used, a current interruption device, FET or IGBT, may be included in each leg 102, 104 and 106 to accommodate switching. Switching elements included in output circuit 100 may alternatively be embodied as other types of switches such as micro electro-mechanical system (MEMs) switches as generally disclosed in commonly assigned U.S. Pat. Appl. Publication No. 2002/0095187 to Thompson et al., hereby incorporated herein by reference in its entirety.

The direction (positive or negative) and width of the pulses generated at output terminals 310, 318, and 320 is controlled by timing algorithms executed by dedicated circuitry in control circuit 230 or by firmware in microprocessor 224 for selectively opening or closing switching elements 112 through 122 in a predetermined pattern to generate a desired phase-shifted waveform.

Figure 3B:
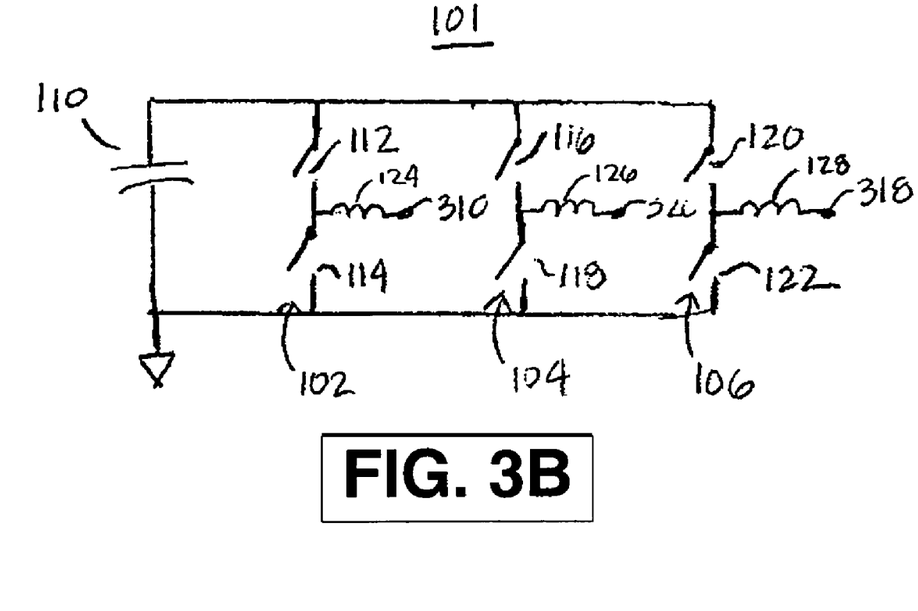
FIG. 3B is a diagram of an alternative output bridge circuit including choke elements.

In one embodiment, pulse width modulation (PWM) is performed to approximate a sinusoidal output from each leg 102, 104 and 106. A smoothed sinusoidal waveform may be produced by passing the PWM signal output of each pair of switching elements 112 and 114, 116 and 118, and 120 and 122 through a "choke" element 124, 126 and 128, respectively, as shown in the modified output bridge circuit 101 of FIG. 3B. Choke elements 124, 126 and 128 may be embodied as inductive circuit components, as shown in FIG. 3B, and serve to smooth the corners of the individual pulses included in a PWM signal to thereby form a smooth sinusoidal signal. While choke elements 124, 126 and 128 are shown in FIG. 3B to be included in bridge circuit 101, choke elements may alternatively be implemented outside bridge circuit 101, for example, in connector block 12 or in the leads carrying the defibrillation electrodes.

However, inductive elements 124, 126, and 128 may not be necessary to achieve reduced energy defibrillation using simultaneously delivered, phase-shifted defibrillation signals and may therefore be eliminated as shown previously in circuit 100 of FIG. 3A. In the embodiment of FIG. 3A, the heart tissue may act as a low pass filter to smooth the pulse width modulated signal to effectively produce a sinusoidal waveform through the defibrillation pathway.

Figure 4:
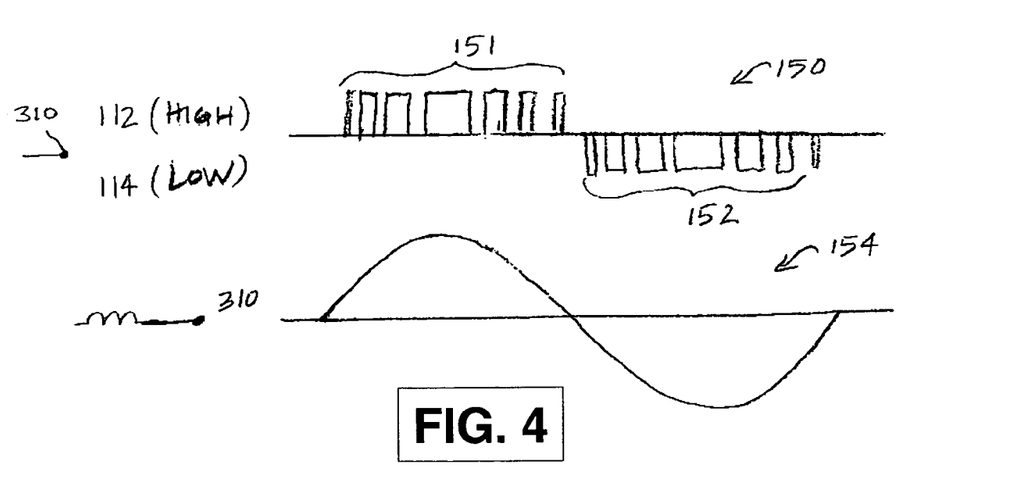
FIG. 4 is a conceptual illustration of a pulse width modulated output signal of any given leg of the output circuit of FIG. 3A, and the resulting sinusoidal waveform after applying a choke as in FIG. 3B.

FIG. 4 is a conceptual illustration of a PWM output signal of any given leg 102, 104, or 106, and the approximated sinusoidal waveform after applying a choke. With reference to leg 102, for example, the output of the "high" switching element 112 produces positive going pulses 151, and output of "low" switching element 114 produces negative going pulses 152 of pulse PWM signal 150. PWM signal 150 is shown containing several positive going pulses 151 and several negative going pulses 152 for the sake of illustration, however, it is recognized that PWM signal 150 may include a much larger number of pulses, for example 128, 256 or 512 pulses, of controlled pulse widths for forming a phasic signal. PWM signal 150 may be delivered to the heart via terminal 310 or smoothed using choke element 123 to deliver smoothed pulses within a sinusoidal envelope and thereby approximate a sinusoidal signal 154 at terminal 310.

Figure 5:
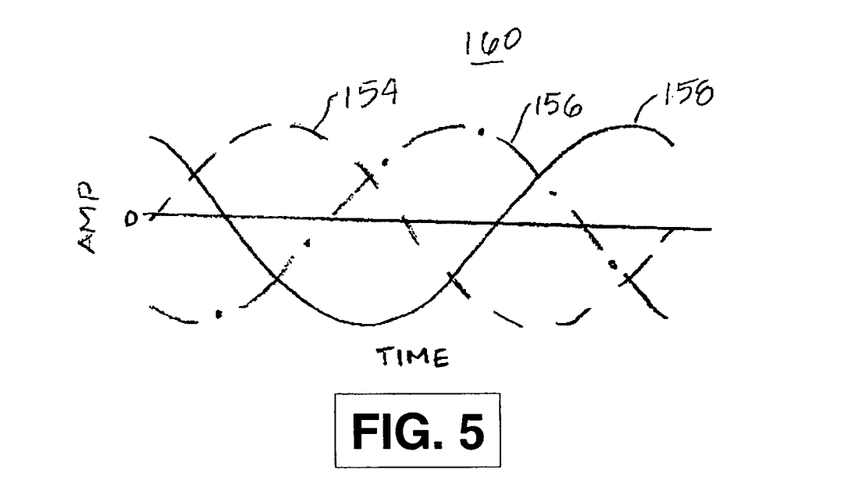
FIG. 5 is a plot of the resultant phase-shifted defibrillation waveform produced by the circuit of FIG. 3B.

FIG. 5 is a plot of the resultant phase-shifted waveform 160 produced by circuit 101. In the same manner as described in conjunction with FIG. 4, switching elements 116 and 118 of leg 104 produce positive and negative going pulses of a PWM signal, which may be smoothed to form an approximate sinusoidal signal 156 at terminal 320, and which is out of phase with sinusoidal signal 154 by a predetermined phase shift. The phase shift between signal 156 and signal 154 is controlled by the timing algorithm controlling the opening and closing of switching elements 116 and 118 and 112 and 114. A phase shift may be, for example, 120 degrees as shown in FIG. 5. Output of switching elements 120 and 122 produce a PWM signal, which is smoothed to form a sinusoidal signal 158, which is phase-shifted, e.g., 120 degrees, with respect to sinusoidal signal 156.

Each signal of the phase-shifted waveform 160 is applied simultaneously to respective electrodes, preferably positioned such that the majority of the targeted heart tissue is encompassed by the geometric space defined by the electrodes. For example, signal 154 may be applied to SVC coil electrode 23; signal 156 may be applied to RV coil electrode 20, and signal 158 may be applied to CS coil electrode 8. The three coil electrodes 8, 20 and 23 are arranged in a triangular manner, which may also be described as a Delta configuration, encompassing a large volume of the cardiac mass. The phase-shifted defibrillation waveform will result in a continuously rotating energy field. The continuous multi-directional field produces a more uniform defibrillation vector field, which is more efficient at depolarizing the heart since a greater mass of cells will be oriented perpendicularly to the energy field (at some point in time during the defibrillation waveform) compared to conventional defibrillation threshold vectors.

The phase-shifted defibrillation waveform may be particularly beneficial in subcutaneous defibrillation applications. Generally higher energy is required for achieving subcutaneous defibrillation than intracardiac defibrillation. The higher delivered voltage during subcutaneous defibrillation may give rise to tissue polarization problems. The lower voltage requirements and rotating field associated with a phase-shifted defibrillation waveform may reduce or eliminate tissue polarization problems that may otherwise be encountered using conventional defibrillation waveforms.

The output of each leg 102, 104, and 106 is shown shifted in phase by 120 degrees in FIG. 5. Phase shifts of greater or less than 120 degrees between each leg 102, 104, and 106 may alternatively be used in achieving a phase-shifted waveform. It is also recognized that while a three-phase waveform is achieved using the three-legged circuitry of FIG. 3A or 3B, additional legs may be provided for delivering four or more phase-shifted signals to four or more pathways.

Figure 6A:
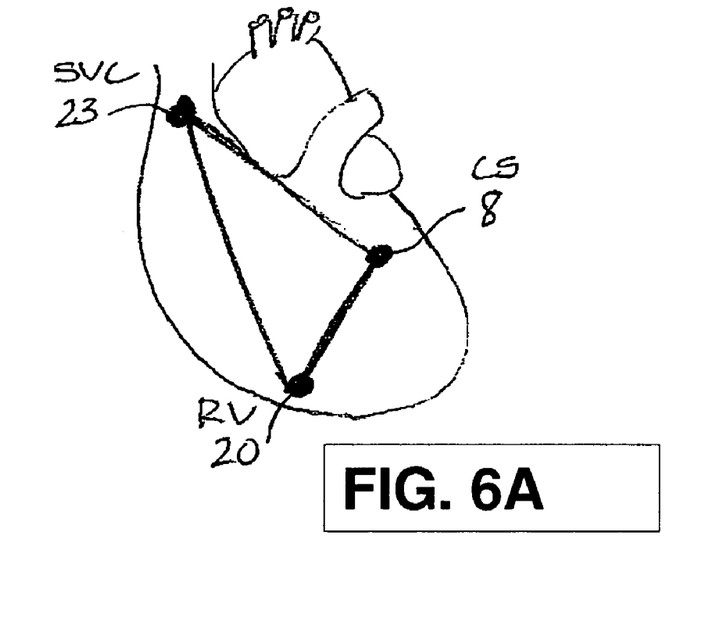
FIGS. 6A and 6B are schematic diagrams illustrating Delta and "Wye" electrode configurations, respectively, that may be used for delivering multi-directional defibrillation waveforms.
Figure 6B:
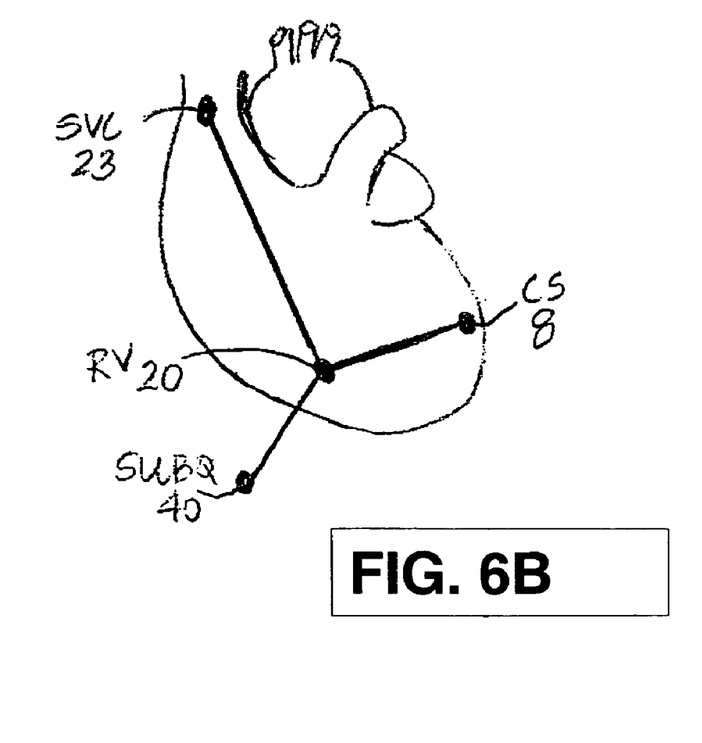

In alternative embodiments, an output bridge circuit may be coupled to defibrillation electrodes arranged in a "Wye" configuration rather than a Delta configuration as described above for delivering phase-shifted defibrillation waveforms. FIGS. 6A and 6B are schematic diagrams illustrating Delta and "Wye" electrode configurations, respectively, that may be used for delivering phase-shifted defibrillation waveforms. As described previously, three electrodes, e.g., RV coil electrode 20, SVC coil electrode 23 and CS coil electrode 8, may be used in a Delta configuration as shown in FIG. 6A. The triangle enclosed by the Delta configuration preferably produces an energy field encompassing a large mass of the targeted heart chambers.

In a "Wye" configuration, as shown in FIG. 6B, four electrodes are required wherein one electrode is the ground return for each of the other legs. In the example shown, the RV coil 20 may be the return electrode for three discharge paths provided by delivering the phase-shifted signals to SVC coil 23, CS coil 8 and a fourth electrode 40, which may correspond to the "CAN" electrode provided by housing 11 or a separately implemented subcutaneous or epicardial electrode. The fourth electrode 40 may be positioned relative to the ventricles so as to provide an additional current pathway not available with the three-electrode Delta configuration. Four-electrode configurations may be implemented using a fourth transvenous, intracardiac electrode as well.

Figure 6C:
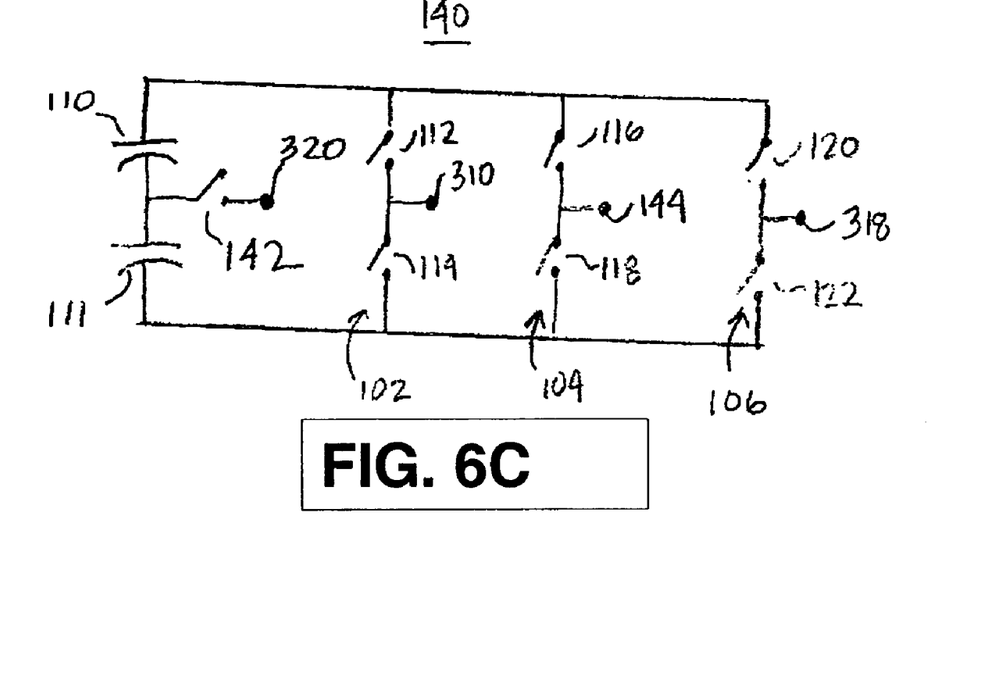
FIG. 6C is a circuit diagram of an output bridge circuit that may be used for achieving the "Wye" configuration shown in FIG. 6B.

FIG. 6C is a circuit diagram of an output bridge circuit that may be used for achieving the "Wye" configuration as shown in FIG. 6B. Output bridge circuit 140 includes an output terminal 320 coupled via a switching element 142 between a pair of capacitor elements 110 and 111. Output terminal 320 provides a common return path for the three legs 102, 104 and 106. Each of legs 102 and 106 include output terminals 310 and 318 coupled between switching elements 112 and 114 and 120 and 122 as described previously. Output leg 104 is shown to include output terminal 144 and switching elements 116 and 118 such that circuit 140 corresponds to the electrode arrangement shown in FIG. 6B. RV coil electrode 20 coupled to output terminal 320 provides a common return path for each of a subcutaneous electrode 40 (coupled to output terminal 144), CS coil electrode 8 (coupled to output terminal 318) and SVC coil electrode 23 (coupled to output terminal 310). Of course other arrangements of electrodes coupled to the output terminals of circuit 140 may be substituted for forming a "Wye" configuration using at least four electrodes.

Figure 6D:
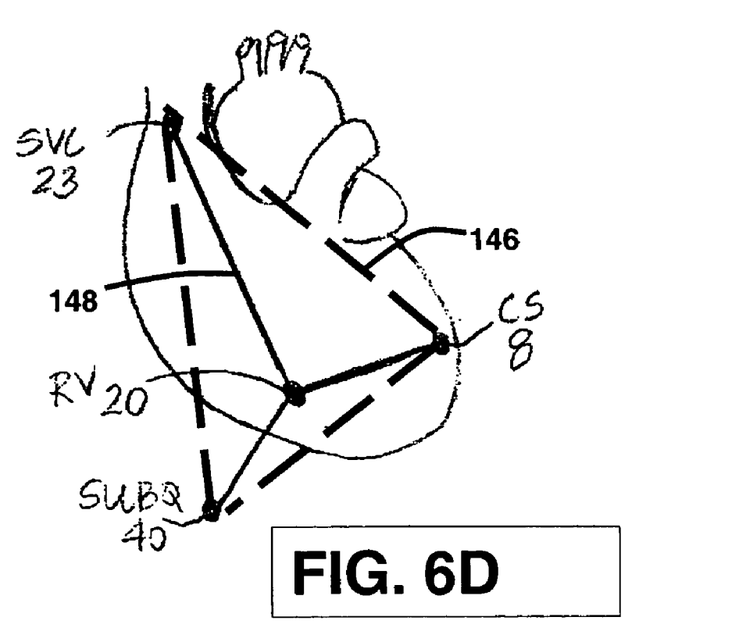
FIG. 6D is a schematic diagram illustrating Delta and "Wye" electrode configurations that may be achieved in alternation using the circuit of FIG. 6C.

By including switching element 142 for coupling output terminal 320 between capacitor elements 110 and 111, circuit 140 may also be used in Delta configuration by opening switching element 142. A. Delta configuration would then exist between output terminal 310 (which may be coupled to SVC coil electrode 23), output terminal 144 (which may be coupled to subcutaneous electrode 40), and output terminal 318 (which may be coupled to CS coil electrode 8). The resulting Delta configuration is shown by dashed line in FIG. 6D. By alternating the state of switching element 142, the output configuration may alternate between a Delta configuration, indicated by dashed line in FIG. 6D, and a "Wye" configuration, indicated by solid lines in FIG. 6D. Thus, a different configuration may be selected for delivering defibrillation waveforms at different times, e.g. in response to different types of arrhythmia detections. Alternatively, the configuration may be alternated between "Wye" and Delta configurations during the delivery of a defibrillation waveform. If an initial shock of a shock sequence fails, the configuration may be changed by changing the state of switching element 142 on a subsequent shock.

Figure 7:
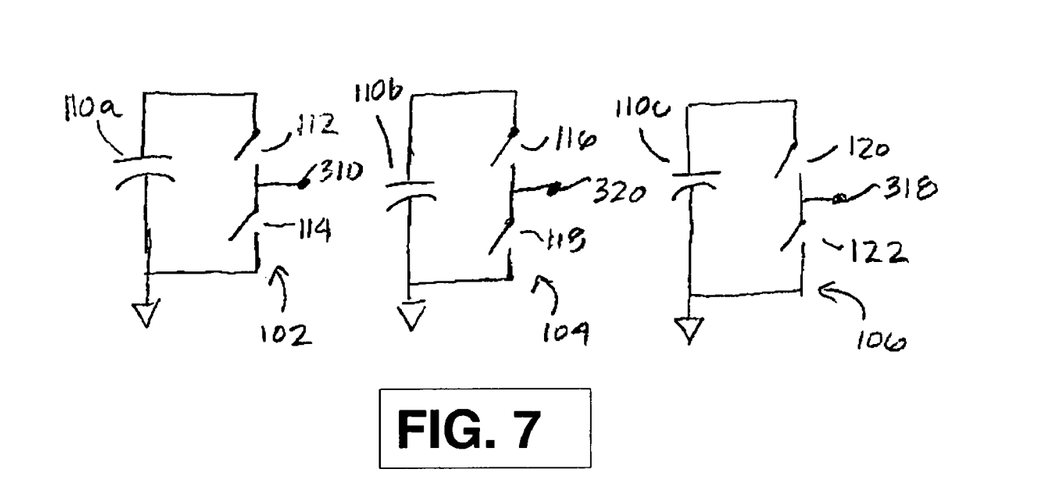
FIG. 7 is a circuit diagram of an alternative embodiment of output circuitry that may be used for delivering multi-directional defibrillation waveforms.

FIG. 7 is a circuit diagram of an alternative embodiment of output circuitry that may be included in output circuit 234. In some embodiments, one or more output legs may be provided, with each of the output legs including a separate designated capacitor to allow different voltage amplitudes to be applied to different output legs. In FIG. 6, each output leg 102, 104 and 106 is provided with a separate capacitor 110a, 110b, and 110c, respectively. While separate capacitors for each output leg are more costly and complex to implement than bridge circuits having only one capacitor, provision of separate voltage signals to each output leg 102, 104, and 106 may allow controlled current steering along the multiple defibrillation pathways. A higher capacitor voltage may be applied to a defibrillation pathway having higher resistance, for example due to a smaller electrode surface area, to obtain a desired current along that pathway. A more uniform or steered multi-directional field may thus be created by controlling the current delivered along the individual pathways.

Figure 8:
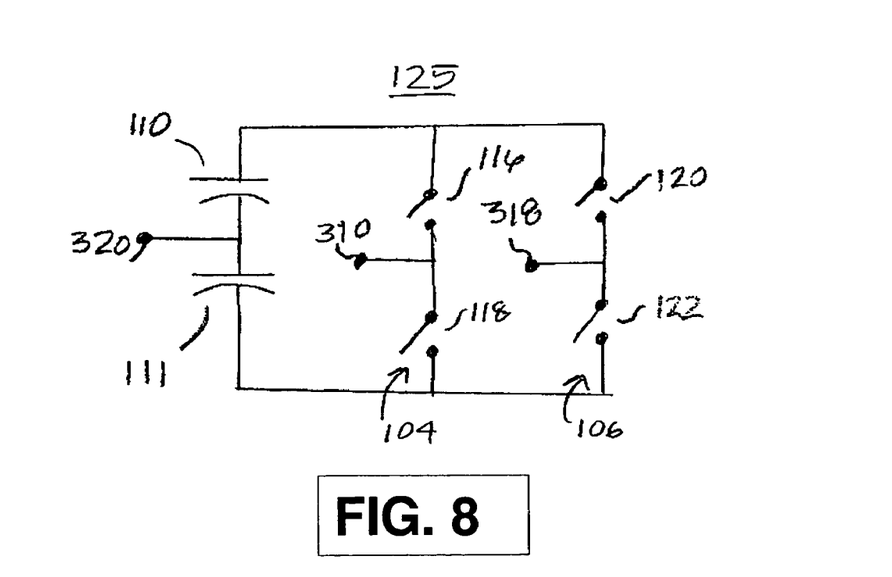
FIG. 8 is a circuit diagram of an alternative embodiment of an output bridge circuit having only two legs of switching circuitry, which may be used for delivering a multi-directional defibrillation waveform.

FIG. 8 is a circuit diagram of an alternative embodiment of an output bridge that may be included in output circuitry 234 for delivering a defibrillation waveform including simultaneously delivered phase-shifted signals for creating a continuous multi-directional vector field. The bridge circuit 125 is simplified by including only two legs of switching circuitry 104 and 106, each with an output terminal 310 and 318, with the third output terminal provided as a reference electrode between two capacitors 110 and 111. Two phase-shifted signals may be delivered to the output terminals 310 and 318 using the third terminal 320 as the return electrode. The two simultaneously delivered phase-shifted signals will produce a multi-directional vector field that will rotate in a continuous, sweeping fashion.

Some of the techniques described above may be embodied as a computer-readable medium comprising instructions for a programmable processor such as microprocessor 224, output circuit 234 or control circuitry 212 shown in FIG. 2. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

Thus, multi-directional defibrillation waveforms may advantageously be implemented in cardioversion/defibrillation devices to realize lower defibrillation thresholds, reduced device size and/or extended useful life. It is recognized that one of skill in the art, having the benefit of the teachings provided herein, may conceive of numerous variations or modifications to the embodiments described herein. For example, different types of continuous phasic signals may be delivered in a phase-shifted manner to a variety of multiple electrode configurations to achieve a continuous multi-directional defibrillation field. Discrete multi-directional defibrillation fields may be created using numerous variations of stepped waveforms delivered to a variety of electrode configurations. Therefore, while specific embodiments have been described to illustrate the various modes for practicing the invention contemplated to date, these illustrative embodiments are intended to be exemplary, rather than limiting with regard to the following claims.

What is claimed is:

1. A medical device for delivering a pulse waveform to a target site of a patient, comprising:
    an energy storage device storing electrical energy;
    a plurality of electrodes electrically coupled to the energy storage device; and
    control circuitry, coupled to the energy storage device and the plurality of electrodes, generating the pulse waveform from the stored energy and delivering the pulse waveform to the target site via the plurality of electrodes, wherein the pulse waveform corresponds to multiple phasic signals delivered simultaneously to multiple pathways between the plurality of electrodes;
    wherein the multiple phasic signals are out of phase by a predetermined phase shift.

2. The device of claim 1, wherein the multiple phasic signals each correspond to a substantially a sinusoidal waveform.

3. The device of claim 1, wherein the predetermined phase shift is approximately equal to 120 degrees.

4. The device of claim 1, further comprising a smoothing element associated with each of the plurality of electrodes to smooth each of the multiple signals.

5. The device of claim 1, wherein the plurality of electrodes are positioned in a Delta configuration about the target site.

6. The device of claim 1, wherein the plurality of electrodes are positioned in a Wye configuration about the target site.

7. The device of claim 1, wherein one or more of the plurality of electrodes is a non-intracardiac electrode.

8. The device of claim 1, wherein one or more of the plurality of electrodes are subcutaneous electrodes.

9. The device of claim 1, further comprising a smoothing element positioned electrically in series with the energy storage device.

10. The device of claim 1, wherein the enemy storage device includes a first element and a second element and the plurality of electrodes includes a reference electrode positioned between the first element and the second element, further comprising:
    a first pair of switching elements associated with a first electrode of the plurality of electrodes to provide a plurality of output pulses corresponding to a first signal of the multiple signals output at the first electrode; and
    a second pair of switching elements associated with a second electrode of the plurality of electrodes to provide a plurality of output pulses corresponding to a second signal of the multiple signals output at the second electrode, wherein the plurality of output pulses corresponding to the first signal and the plurality of output pulses corresponding to the second signal each include positive going and negative going pulses forming a bipolar signal, and wherein the first signal and the second signal are out of phase by a predetermined phase shift.

11. A medical device for delivering a pulse waveform comprising multiple signals to a target site of a patient, comprising:
    an energy storage device storing electrical energy;
    a plurality of electrodes electrically coupled to the energy storage device;
    a first pair of switching elements associated with a first electrode of the plurality of electrodes to provide a plurality of output pulses corresponding to a first signal of the multiple signals output at the first electrode;
    a second pair of switching elements associated with a second electrode of the plurality of electrodes to provide a plurality of output pulses corresponding to a second signal of the multiple signals output at the second electrode;
    a third pair of switching elements associated with a third electrode of the plurality of electrodes to provide a plurality of output pulses corresponding to a third signal of the multiple signals output at the third electrode; and
    control circuitry controlling the switching elements in a predetermined pattern to generate the pulse waveform as multiple phasic signals delivered simultaneously to multiple pathways associated with the plurality of electrodes;
    wherein the multiple phasic signals are out of phase by a predetermined phase shift.

12. The device of claim 11, wherein the plurality of output pulses corresponding to the first signal, the plurality of output pulses corresponding to the second signal, and the plurality of output pulses corresponding to the third signal each include positive going and negative going pulses forming a phasic signal corresponding to a substantially sinusoidal waveform.

13. The device of claim 11, further comprising:
a first smoothing element to smooth the plurality of output pulses corresponding to the first signal;
a second smoothing element to smooth the plurality of output pulses corresponding to the second signal; and
a third smoothing element to smooth the plurality of output pulses corresponding to the third signal.

14. The device of claim 11, wherein the energy storage device includes a first element and a second element, and further comprising:
an output switching element coupled to the control circuitry between the first element and the second element, wherein the control circuitry controls a state of the output switching element to alternate the between a Delta configuration and a Wye configuration.

15. The device of claim 11, wherein the energy storage device includes a first energy storage element associated with the first switching element, a second energy storage element associated with the second switching element, and a third energy storage element associated with the third switching element.

16. The device of claim 11, further comprising a smoothing element positioned electrically in series with the energy storage device.

17. A method of delivering a pulse waveform to a target site of a patient, comprising:
generating a plurality of output pulses corresponding to each of a plurality of electrodes; and
controlling switching elements associated with each of the plurality of electrodes in a predetermined pattern to generate the pulse waveform as multiple phasic signals delivered simultaneously to multiple pathways associated with the plurality of electrodes;
wherein the multiple phasic signals are out of phase by a predetermined phase shift.

18. The method of claim 17, wherein the multiple phasic signals each correspond to a substantially sinusoidal waveform.

19. The method of claim 17, wherein the predetermined phase shift is approximately equal to 120 degrees.

20. The method of claim 17, wherein the plurality of electrodes are approximately positioned in a Delta configuration about the target site.

21. The method of claim 17, wherein the plurality of electrodes are positioned in a Wye configuration about the target site.

22. The method of claim 17, wherein one or more of the plurality of electrodes is a non-intracardiac electrode.

23. The method of claim 17, wherein one or more of the plurality of electrodes are subcutaneous electrodes.

24. A computer-readable medium having computer-executable instructions for performing a method, comprising:
generating a plurality of output pulses corresponding to each of a plurality of electrodes; and
controlling switching elements associated with each of the plurality of electrodes in a predetermined pattern to generate the pulse waveform as multiple phasic signals delivered simultaneously to multiple pathways associated with the plurality of electrodes;
wherein the multiple phasic signals are out of phase by a predetermined phase shift.

* * * * *

UNITED STATES PATENT AND TRADEMARK OFFICE
CERTIFICATE OF CORRECTION

| | | |
|---|---|---|
| PATENT NO. | : 7,136,702 B2 | |
| APPLICATION NO. | : 10/804322 | |
| DATED | : November 14, 2006 | |
| INVENTOR(S) | : Wanasek | |

It is certified that error appears in the above-identified patent and that said Letters Patent is hereby corrected as shown below:

Column 14, line 14, please delete "the enemy storage" and insert --the energy storage--

Signed and Sealed this

Fifteenth Day of May, 2007

JON W. DUDAS
*Director of the United States Patent and Trademark Office*